United States Patent [19]

Potter et al.

[11] 4,438,212

[45] Mar. 20, 1984

[54] FLUORINE-FREE CALCIUM-ALUMINOSILICATE GLASSES

[75] Inventors: William D. Potter, Bishops Stortford; Andrew C. Barclay, Harlow; Reginald Dunning, Parbold near Wigan; Richard J. Parry, Southport, all of England

[73] Assignee: Pilkington Brothers P.L.C., England

[21] Appl. No.: 392,668

[22] Filed: Jun. 28, 1982

[30] Foreign Application Priority Data

Jul. 3, 1981 [GB] United Kingdom ............... 8120581

[51] Int. Cl.³ .................. C03C 3/04; C03C 12/00
[52] U.S. Cl. ............................. 501/73; 128/90; 501/77
[58] Field of Search ............ 501/73, 28, 77; 128/90; 260/998.11

[56] References Cited

U.S. PATENT DOCUMENTS

| | | | |
|---|---|---|---|
| 3,531,306 | 9/1970 | Dumbaugh | 501/73 |
| 3,822,799 | 7/1974 | Evans | 501/28 |
| 4,108,169 | 8/1978 | Parker | 128/90 |
| 4,137,086 | 1/1979 | Potter et al. | 501/73 |
| 4,376,835 | 3/1983 | Schmitt et al. | 501/73 |
| 4,401,773 | 8/1983 | Smyth | 523/116 |

OTHER PUBLICATIONS

Maratheu, A. et al., "Utilisation de Laitiers Sidérurgiques pour la Fabrication de Carreaux de Faience"–L-'Industrie Ceramique, Jun. 1969, No. 619, pp. 405–414.

*Primary Examiner*—Helen M. McCarthy
*Attorney, Agent, or Firm*—Jacobs & Jacobs

[57] ABSTRACT

The invention relates to calciumaluminosilicate glasses. The glasses contain, in weight percent, 25 to 35% silica, 27 to 35% calcium oxide, 25 to 40% alumina, 0 to 4% of alkali metal oxide selected from lithium oxide, sodium oxide and potassium oxide, and 0 to 5% of titanium oxide and a total content of lithium, sodium, potassium and titanium oxides of 0.5 to 9%. The glasses, in finely divided form, react with aqueous polycarboxylic acids and set to a solid mass; cements made from the glass and polycarboxylic acids are useful in splinting compositions.

10 Claims, No Drawings

FLUORINE-FREE CALCIUM-ALUMINOSILICATE GLASSES

BACKGROUND OF THE INVENTION

1. Field of the Invention

This invention relates to calcium aluminosilicate glasses which, in finely divided form, react with aqueous polycarboxylic acids and set to form a solid mass. Cements formed from glasses of the invention and polycarboxylic acids are particularly suitable for use in splinting agents.

2. Description of the Prior Art

It is now well established that splinting bandages can be prepared from water hardenable cement compositions in which the reactive components are a glass and a polycarboxylic acid. The most successful version of this form of bandage is described in British Pat. No. 1,554,554 and the glasses used in the cements are described in British Pat. No. 1,554,555. One example of such a bandage using such a glass is available as "CRYSTONA" from T. J. Smith & Nephew of Welwyn Garden City and Hull, U.K. This existing product has many excellent properties resulting from the use of a calcium fluoroaluminosilicate glass, as described in British Pat. Nos. 1,554,554/5, to provide a composition which remains workable for a period (the gel time) sufficient to enable the bandage to be placed in position, but then sets quite rapidly. Unfortunately the need to incorporate quantities of fluorine in the glass to achieve an acceptable gel time and set time adds substantially to the cost of the production process. This is because fluorine is regarded as an atmospheric pollutant and glasses containing significant quantities of fluorine need to be made under strictly controlled and hence expensive operating conditions in order to protect the environment.

SUMMARY OF THE INVENTION

Glasses have now been discovered which do not require the presence of fluorine in order to achieve a desirable combination of gel and set times in a cement composition.

Accordingly the present invention provides a calciumaluminosilicate glass containing 25 to 35% silica, 27 to 35% calcium oxide, 25 to 40% alumina, 0 to 4% of alkali metal oxide selected from lithium oxide, sodium oxide and potassium oxide, and 0 to 5% of titanium oxide with the proviso that the total amount of lithium, sodium, potassium and titanium oxide is 0.5 to 9%.

All percentages herein are on a weight/weight basis unless otherwise stated.

As is conventional in the glass making art the glasses of this invention may also contain small quantities of compatible materials which do not affect the melting or performance of the glass to an unacceptable extent. Generally the presence of such other agents is not envisaged as desirable and preferably the glass is free of fluorine containing materials.

The glasses may be used, in finely divided form, in conjunction with polycarboxylic acids to form water-hardenable cement compositions. Such cements have a sufficiently long gel time, in combination with a short set time, to make them useful in surgical splinting and, unlike the glasses described in U.K. Pat. No. 1,554,555, do not contain fluorine as an essential constituent.

DETAILED DESCRIPTION OF THE INVENTION

Favoured glasses of this invention include those which contained in total from 1.5 to 5% of the alkali metal and titanium oxides. Moreover, sodium oxide is generally the preferred alkali metal oxide.

For ease of melting, it is preferred that the glasses contain 28 to 34% silica, 28 to 34% calcium oxide and 30 to 40% alumina.

From the foregoing it will be appreciated that certain especially favoured glasses of this invention are those containing 28 to 34% silica, 28 to 34% calcium oxide, 30 to 40% alumina and 0 to 4% of sodium oxide and 0 to 5% of titanium oxide with the proviso that the total amount of sodium and titanium oxides is 1.5 to 5%.

Preferably if the glass of this invention is free of sodium, potassium and lithium oxides then it will contain 1 to 4% titanium oxide. Preferably if the glass of this invention is free of titanium oxide it will not contain more than 3% in total of sodium, potassium and lithium oxides.

Aptly the glasses of this invention will contain calcium oxide and silica in a ratio of 0.7:1 to 1:0.7, more suitably 0.8:1 to 1:1.1 and preferably about 0.9:1 to 1:1.

Certain preferred glasses of this invention consist essentially of 30 to 34% silica, 28 to 33% calcium oxide, 32 to 40% alumina and 1 to 3% of sodium oxide.

For use in cements the glasses of this invention will be in finely divided form. Aptly the glasses will have a surface area of 1250 to 2000 cm$^2$/g and more aptly 1500 to 1850 cm$^2$/g. Normally the finely divided glass will be in the form of a finely divided powder. Generally the individual particles will be less than 100 microns and preferably less than 50 microns.

The glasses of this invention may be prepared by melting together silica, alumina, calcium oxide and the required alkali metal and/or titanium oxide in the previously described amounts. If desired precursors of such oxides may be employed. Generally melting of the mixtures occurs within the range 1350° C. to 1600° C., with the especially favoured glasses referred to above melting generally towards the lower end of this temperature range.

After solidification on cooling the glass can be converted to the desired finely divided form in conventional manner such as ball milling, pestle-and-mortar grinding or the like with sieving if desired.

The glass in its finely divided form may be mixed with polycarboxylic acid or a polymeric precursor thereof for example a polycarboxylic acid anhydride for use as a water-hardenable cement position.

The polycarboxylic acids used in the cements may be homopolymers of unsaturated monocarboxylic acids or unsaturated dicarboxylic acids or copolymers between any two or more of these acids or copolymers of one or more of these acids with one or more other ethylenically unsaturated monomers. Suitable unsaturated carboxylic acids for the present invention include acrylic, itaconic, mesaconic, citraconic, or maleic acids. The preferred polycarboxylic acid is the homopolymer of acrylic acid which will be referred to hereinafter as polyacrylic acid.

The polyacrylic acid for use in the cement will normally have a molecular weight of from 1000 to 1,000,000. Polyacrylic acids having a molecular weight of 50,000 to 500,000 are preferred.

Suitably the polycarboxylic acid forms 20 to 30% of the dry composition. More suitably the polycarboxylic acid forms 22 to 28% of the composition. Preferably the polycarboxylic acid forms 23 to 25% of the composition.

Usually the cement compositions incorporating the glasses of this invention will include a monomeric acid containing at least two carboxyl groups or a hydroxy carboxylic acid. The presence of an acid of this type serves to maximise the desirable properties of the composition of this invention with regard to gel time and set time. Suitable organic acids include tartaric, succinic, oxalic, citric and ascorbic acids. The preferred acid is tartaric acid.

A particularly suitable amount of this acid to be present in cement compositions containing the glasses of the invention is 1 to 4% and is preferably 2%.

Usually the dry cement compositions incorporating the glass and polycarboxylic acid will include 5 to 10% of sodium chloride to improve the shrinkage characteristics of the composition while setting. More suitably the composition will contain 6 to 8% of sodium chloride. Preferably about 7% of sodium chloride is employed.

Usually a thickening agent will be employed in cement compositions incorporating the glasses of the present invention. Suitable thickening agents include cellulose derivatives or a modified bentonite clay. Preferred thickening agents are hydroxypropylcellulose or a modified bentonite clay or a mixture thereof.

Thickening agents will suitably comprise up to 4% of the cement compositions and preferably will comprise 1 to 3% of the compositions.

Generally the cement compositions will include a particulate material as a filler. Suitably alumina may be used as a filler without causing undue weakening of the set cements which are formed from the composition. Most suitably 25 to 35% of alumina may be used in the composition. More favourably 27 to 32% and preferably 28.4% of alumina is used in the composition.

The various components of the water-hardenable cement composition are generally provided in the form of fine particles. The particle size of the finely divided glass has been described above. The polyacrylic acid particle size will generally be in the range 5 to 150 microns and more suitably in the range 10 to 100 microns. The organic acid and sodium chloride particles will generally be in the size range 2 to 70 microns. The alumina particles will have a mean specific surface area of powder greater than 15,000 cm$^2$/g and preferably greater than 20,000 cm$^2$/g with at least 80% of the particles less than 10 microns and preferably 90% of the particles are less than 10 microns in size.

The various components of the cement composition may be blended together in a conventional manner, for example by dry powder blending.

When water is added to a cement composition as described above it will first gel and then set. It has been found that to give desirable properties for use on a carrier as a splinting bandage the gel time is suitably in the range 65 to 130 seconds and is preferably in the range 80 to 120 seconds. The corresponding set time is suitably in the range from 5 to 18 minutes and preferably is from 10 to 15 minutes. As the gel time and set time may vary independently of each other as the components of the composition vary it is convenient to consider the set time to gel time ratio as a criterion of acceptability for use in a splinting bandage. It is preferred that this ratio lies in the range of 6:1 to 14:1 and preferably is in the range 7:1 to 10:1.

From the foregoing it will be appreciated that favoured water-hardenable cement compositions consist essentially of 34 to 38% of a calcium aluminosilicate glass, 23 to 25% of a polycarboxylic acid, 27 to 32% of alumina, 6 to 8% sodium chloride, 1 to 4% organic acid, 1 to 3% as a thickener of a mixture of hydroxypropylcellulose and modified bentonite clay.

A preferred water-hardenable cement composition comprises 36.3% of a calcium aluminosilicate glass, 24.3% polyacrylic acid, 28.4% alumina, 7% sodium chloride, 2.0% tartaric acid, 1.65% hydroxypropyl cellulose and 0.35% of a modified bentonite clay.

Although the water-hardenable cement compositions may be used for a wide range of cement purposes, they are of particular use in the preparation of splinting materials.

For use in splinting, the cement composition is loaded on a carrier, normally an openwork substrate (woven or non-woven) of which a Leno gauze of polyester and cotton is preferred. Loading may be by way of coating or impregnation using, for example a slurry of the water-hardenable cement composition in a volatile organic liquid and thereafter removing the volatile organic liquid by evaporation.

The organic liquid can be any unreactive liquid which does not cause gellation and which may be removed by evaporation. A preferred liquid is methylene chloride. Normally the weight of methylene chloride used is about half the weight of water-hardenable cement composition.

The splinting material is generally in the form of a bandage provided rolled on a support core, for example a cruciform core, so that in use it is dipped into water for a few seconds, squeezed and wrapped around the affected limb or the like and allowed to gel and set to a hard material.

It will be appreciated that, when the cement compositions of glass and polyacrylic acids are used in products other than splinting materials, it may be desirable to vary the nature and amounts of any additional components used.

EXAMPLE 1

Calcium Aluminosilicate Glass

A calcium aluminosilicate glass was prepared from the following ingredients:

| | |
|---|---|
| Silica | 250.8 g |
| Calcium carbonate | 410.3 g |
| Aluminum hydroxide | 466.8 g |
| Sodium carbonate | 24.35 g | to give a glass of the following composition expressed as % w/w

| | |
|---|---|
| Silica | 31.4% |
| Calcium oxide | 28.7% |
| Alumina | 38.1% |
| Sodium oxide | 1.8% |

The ingredients were melted in a crucible at 1500° C. and when molten stirred. The molten glass was then poured into water.

EXAMPLE 2

Grinding of Calcium Aluminosilicate Glass

A portion of calcium aluminosilicate glass prepared in Example 1 was taken and ground in a mechanical pestle and mortar for one hour. Suitable mechanical pestle and mortars are available from the Pascall Engineering Co. Ltd. The powder obtained was sieved through a coarse sieve to remove the largest particles of glass and the remaining powder was re-sieved and the fraction having a particle size less than 45 microns was isolated for use in a water-hardenable cement composition.

EXAMPLE 3

Water-hardenable Cement Composition

A water-hardenable cement composition was formulated as follows:

| | |
|---|---|
| Calcium aluminosilicate glass of Example 2 | 36.3% |
| Polyacrylic acid | 24.3% |
| Alumina | 28.4% |
| Sodium chloride | 7.0% |
| Tartaric acid | 2.0% |
| Hydroxypropyl cellulose | 1.65% |
| Modified bentonite clay | 0.35% |

The dry particulate materials were mixed and a portion taken to be assessed for gel and set time. To determine gel time and set time, water at 20° C. was added to a container such that the ratio of water to powder was 1:2 by weight. A portion of the homogeneous wet mix was poured into a cylindrical mould of 25.4 mm internal diameter, 2 mm deep, resting on a glass plate, all the apparatus being kept at 20° C. and in an atmosphere having a relative humidity of 65%. The portion of the mix in the container was used to determine the gel time. The composition was deemed to have gelled when on gentle manipulation with a spatula the composition failed to flow from the end of the spatula. The gel time extended from the time of mixing until gelling. The composition was deemed to have set when a Gilmore "final" needle (of weight 454 g, diameter 1.06±0.05 mm, cylindrical for 4.8 mm from its plane end at right angles to the rod) lowered vertically onto the horizontal surface in the mould and allowed to rest thereon for approximately five seconds left no perceptible indentation. The set time extended from mixing to setting. Each timing was repeated three times and an average value taken.

The gel time of this composition was 94 seconds and the set time 12.1 minutes to give a set to gel time ratio of 7.7.

EXAMPLE 4

Water-Hardenable Cement Bandage

A bandage useful for a splinting application was prepared using a portion of the water-hardenable cement composition described in Example 3.

Hydroxypropyl cellulose (2%) was dissolved in methylene chloride. The dry particulate water-hardenable cement composition was added to this solution until on mixing a slurry was formed which had a solids content of 50%.

The slurry was placed in an application box with a flexible doctor blade and ridging bar and spread at a loading of 300 g/m$^2$ of a Leno gauze bandage of cotton polyester weave about 9 meters long and 8 cm wide. The bandage was air dried and wrapped around a conventional cruciform core.

EXAMPLES 5 TO 24

Calcium aluminosilicate glasses were prepared as in Example 1 and water-hardenable cement compositions prepared and tested as described in Examples 2 and 3. The following Table describes the composition and properties of these glasses.

TABLE

| Example | Silica | Calcium oxide | Alumina | Sodium oxide | Titanium oxide | additional constituents | Gel (secs) | Set (mins) | Set time / Gel time |
|---|---|---|---|---|---|---|---|---|---|
| 5 | 33.2 | 29.9 | 35.0 | 1.8 | 0 | | 70 | 10.4 | 8.9 |
| 6 | 31.3 | 29.3 | 37.5 | 1.8 | 0 | | 107 | 14.7 | 8.2 |
| 7 | 31.0 | 29.8 | 36.2 | 1.8 | 1.2 | | 132 | 18 | 8.2 |
| 8 | 33.1 | 29.8 | 34.8 | 0 | 2.3 | | 142 | 20 | 8.5 |
| 9 | 32.0 | 31.8 | 33.9 | 0 | 2.3 | | 116 | 16.2 | 8.4 |
| 10 | 31.1 | 29.0 | 37.2 | 2.7 | 0 | | 81 | 11.2 | 8.3 |
| 11 | 30.5 | 29.3 | 35.5 | 3.6 | 1.1 | | 70 | 11.2 | 9.6 |
| 12 | 32.5 | 29.2 | 34.2 | 1.8 | 2.3 | | 94 | 13.6 | 8.7 |
| 13 | 31.3 | 32.0 | 32.5 | 1.8 | 2.4 | | 84 | 10.1 | 7.2 |
| 14 | 30.4 | 31.9 | 32.4 | 1.8 | 3.4 | | 118 | 15.3 | 7.8 |
| 15 | 29.4 | 31.8 | 32.4 | 1.8 | 4.7 | | 157 | 22 | 8.5 |
| 16 | 33.9 | 33.3 | 30.4 | 0 | 2.4 | | 92 | 12.1 | 7.9 |
| 17 | 28.8 | 33.0 | 30.1 | 0 | 3.0 | 5.1 B$_2$O$_3$ | 98 | 17.5 | 10.7 |
| 18 | 33.2 | 29.9 | 35.0 | 0 | 1.8 | 0 | 70 | 10.4 | 8.9 |
| 19 | 31.7 | 29.6 | 37.9 | 0.9 | 0 | 0 | 89 | 17.0 | 11.5 |
| 20 | 30.8 | 28.8 | 36.8 | 3.6 | 0 | 0 | 65 | 8.1 | 7.5 |
| 21 | 31.2 | 28.6 | 38.0 | 0.9 | 0 | 1.4 K$_2$O | 47 | 11.0 | 14.0 |
| 22 | 31.6 | 29.0 | 38.5 | 0 | 0 | 0.9 Li$_2$O | 85 | 12.3 | 8.7 |
| 23 | 31.1 | 28.5 | 37.8 | 0 | 0 | 2.7 K$_2$O | 61 | 9.0 | 8.9 |
| 24 | 31.4 | 28.1 | 40.0 | 0.5 | 0 | 0 | 80 | 9.6 | 7.2 |

We claim:

1. A fluorine-free calciumaluminosilicate glass consisting essentially of 25 to 35% silica, 27 to 35% calcuim oxide, 25 to 40% alumina, 0 to 4% of alkali metal oxide selected from lithium oxide, sodium oxide and potassium oxide, and 0 to 5% of titanium oxide with a total content of lithium, sodium, potassium and titanium oxides of 0.5 to 9%, and with a ratio of calcium oxide to silica of 0.7:1 to 1.0:0.7, said glass being in particulate form in which the individual particles have a particle size of less than 100 microns.

2. A glass as claimed in claim 1 containing in total from 1.5 to 5% of the alkali metal and titanium oxides.

3. A glass as claimed in claim 1 containing 28 to 34% silica, 28 to 34% calcium oxide and 30 to 40% alumina.

4. A glass as claimed in claim 1 which is free from sodium, potassium and lithium oxides and contains 1 to 4% titanium oxide.

5. A glass as claimed in claim 1 which is free of titanium oxide and contains 1.5 to 3% in total of sodium, potassium and lithium oxides.

6. A glass as claimed in claim 1 containing calcium oxide and silica in a ratio of 0.8:1 to 1:1.1.

7. A glass as claimed in claim 1 containing calcium oxide and silica in a ratio of 0.9:1 to 1:1.

8. A glass as claimed in claim 1 consisting essentially of 30 to 34% silica, 28 to 33% calcium oxide, 32 to 40% alumina and 1 to 3% sodium oxide.

9. A fluorine-free calciumaluminosilicate glass consisting essentially of 28 to 34% silica, 28 to 34% calcium oxide, 30 to 40% alumina and 0 to 4% of sodium oxide and 0 to 5% of titanium oxide with a total content of sodium and titanium oxides of 1.5 to 5%, said glass being in particulate form in which the individual particles have a particle size of less than 100 microns.

10. A fluorine-free calciumaluminosilicate glass consisting essentially of 30 to 34% silica, 28 to 33% calcium oxide, 32 to 40% alumina and 1 to 3% sodium oxide, and being in particulate form in which the individual particles have a particle size of less than 100 microns.

* * * * *